United States Patent
Feldstein et al.

(10) Patent No.: US 6,210,931 B1
(45) Date of Patent: Apr. 3, 2001

(54) RIBOZYME-MEDIATED SYNTHESIS OF CIRCULAR RNA

(75) Inventors: Paul A. Feldstein, Davis, CA (US); Robert A. Owens; Laurene Levy, both of Beltsville, MD (US); John W. Randles, Stirling (AU)

(73) Assignee: The United States of America as represented by the Secretary of Agriculture, Washington, DC (US)

( * ) Notice: Subject to any disclaimer, the term of this patent is extended or adjusted under 35 U.S.C. 154(b) by 0 days.

(21) Appl. No.: 09/200,955

(22) Filed: Nov. 30, 1998

(51) Int. Cl.[7] ........................................ C12P 19/34
(52) U.S. Cl. ..................... 435/91.1; 435/69.1; 435/6; 435/91.21; 435/91.31; 435/91.4; 435/91.42; 435/172.1; 435/172.3; 436/503; 536/23.1
(58) Field of Search ............................. 435/91.1, 69.1, 435/91.21, 91.3, 91.31, 91.4, 91.42, 172.1, 172.3, 253.3, 254.2, 254.21, 320.1, 6, 7.21; 436/503, 813, 518; 536/23.1

(56) References Cited

U.S. PATENT DOCUMENTS

| | | | |
|---|---|---|---|
| 4,101,401 | * | 7/1978 | Hoefer et al. ........................ 204/180 |
| 4,338,397 | * | 7/1982 | Gilbert et al. ......................... 435/68 |
| 5,298,135 | * | 3/1994 | Geoghehan et al. .............. 204/182.8 |
| 5,607,833 | * | 3/1997 | Gilman et al. ........................... 435/6 |
| 5,625,047 | * | 4/1997 | Been et al. .......................... 536/23.1 |
| 5,762,937 | * | 6/1998 | Atkinson et al. .................. 424/198.1 |
| 5,773,244 | * | 6/1998 | Ares, Jr. et al. ..................... 435/69.1 |
| 5,865,975 | * | 2/1999 | Bishop et al. ........................ 204/618 |
| 5,883,228 | * | 3/1999 | Darnell, Jr. et al. ................. 530/350 |

* cited by examiner

Primary Examiner—W. Gary Jones
Assistant Examiner—Janell Taylor
(74) Attorney, Agent, or Firm—M. Howard Silverstein; John D. Fado; Janelle S. Graeter (57) ABSTRACT

Circular RNAs may be synthesized by inserting DNA fragments into a plasmid containing sequences having the capability of spontaneous cleavage and self-circularization. Insertion of the DNA fragments allows RNAs of predetermined size to be constructed. In addition, a two-dimensional polyacrylamide gel electrophoresis system having a second dimension more highly cross-linked than the first dimension permits the separation and analysis as well as the precise sizing of both linear and circular RNAs produced by the synthetic method.

6 Claims, 4 Drawing Sheets

SEQUENCE LISTING

<160> NUMBER OF SEQ ID NOS: 3

<210> SEQ ID NO 1
<211> LENGTH: 102
<212> TYPE: RNA
<213> ORGANISM: Tobacco ringspot virus

<400> SEQUENCE: 1
guccuguccg uaugacagag aagucaacca gagaaacaca cguuguggua uauuaccugg      60
uacccgggga uccucuagag ucgaccugca ggggcccuga cc                       102

<210> SEQ ID NO 2
<211> LENGTH: 17
<212> TYPE: DNA
<213> ORGANISM: Unknown
<220> FEATURE:
<223> OTHER INFORMATION: Description of Unknown Organism:M13 universal
      forward primer

<400> SEQUENCE: 2
gtaaaacgac ggccagt                                                    17

<210> SEQ ID NO 3
<211> LENGTH: 16
<212> TYPE: DNA
<213> ORGANISM: Unknown
<220> FEATURE:
<223> OTHER INFORMATION: Description of Unknown Organism:M13 universal
      reverse primer

<400> SEQUENCE: 3
caggaaacag ctatga                                                     16

RIBOZYME-MEDIATED SYNTHESIS OF CIRCULAR RNA

BACKGROUND OF THE INVENTION

1. Field of the Invention

Molecular markers are conventionally used in the electrophoretic separation and/or identification of microbiological materials. During polyacrylamide gel electrophoresis (PAGE) under denaturing conditions, circular RNAs usually migrate more slowly than the corresponding linear molecules, therefore an accurate system must accomodate both types of molecules. This invention relates to a novel method for the preparation of circular RNAs useful as markers and to an electrophoretic system capable of allowing the precise sizing of both linear and circular RNA molecules.

2. Description of the Related Art

Circular RNAs have been shown to play an active role in a number of important biological processes such as the infection of a number of plants. For example, the potato spindle tuber viroid, a small autonomously replicating pathogenic RNA, was the first reported naturally-occurring circular RNA. Subsequently, other covalently circular subviral RNAs were reported, including the satellite RNA of tobacco ringspot virus, satTRSV RNA (Sogo and Schneider. 1982. *Virology.* vol. 117, pp. 401–415) and the genome of hepatitis delta virus (Wang et al. 1986. *Nature.* vol. 323, pp. 508–514).

Circular RNAs are also generated by synthesis and processing of cellular mRNAs and rRNAs. For example, following self-excision from pre-rRNA, the group I intron of *Tetrahymena thermophila* circulizes via attack of its 3'-terminal hydroxyl group on a phosphodiester linkage near the 5'-terminus (see, for example, Kruger et al. 1982. *Cell.* vol. 31, pp. 147–157). In addition, spliceosome-mediated maturation of eukaryotic mRNA as well as self-excision of group II introns releases a branched or "lariat" RNA in which the 5'-terminus of the intron is joined to the free 2'-OH of an adenylate residue ~25 nt upstream from the 3' splice site (reviewed in Padgett et al. 1986. *Annu. Rev. Biochem.* vol. 55, 1119–1150; Ferat and Michel. 1995. *Annu. Rev. Biochem.* vol. 64, pp. 435–461). Splice site pairing across an exon can also result in exon circularization in vitro (Pasman et al. 1996. *RNA.* vol. 2, pp. 603–610). These circularized RNAs have been found to be more resistant to degradation than the corresponding linear forms (Puttaraju et al. 1993. *Nucleic Acids Res.* vol. 21, pp. 4253–4258).

Production of circular RNAs has been attempted by various methods; however, in general, the process is complicated and requires extensive purification. Wang and Kool (1994. *Nucleic Acids Research.* vol. 22, no. 12, pp. 2326–2333), for example, disclosed a nonenzymatic synthetic method for the production of circular RNA oligonucleotides utilizing preparative 20% denaturing PAGE for purification purposes. Beaudry and Perrault (1995. *Nucleic Acids Research.* vol. 23, no. 15, pp. 3064–3066) described a synthetic method which involved PCR amplification of a particular gene sequence of unit length. It was considered an improvement over conventional techniques because it required only one purification step.

A number of electrophoresis systems capable of resolving circular and linear RNA have been described, but preparation of the molecular standards necessary for calibrating the gels can be laborious (e.g., Maniatis et al. 1975. *Biochemistry.* vol. 14, pp. 3787–3794; Singh and Boucher. 1987. *Phytopathology.* vol. 77, pp. 1588–1591; Schumacher et al. 1983. *Anal. Biochem.* vol. 135, pp. 288–295; Schumacher et al. A986. *J. Phytopathol.* vol. 115, 332–343).

An improved method which simplifies the preparation of circular RNAs for use as markers in PAGE systems and for a simplified PAGE system which accurately separates and identifies circular and linear RNAs would be advantageous in studies requiring accurate sizing of naturally-occurring linear and circular pathogenic RNAs associated with both animal and plant diseases and the abnormal processing of cellular messenger RNAs.

SUMMARY OF THE INVENTION

In satTRSV(-)RNA, the complementary form of satTRSV RNA, spontaneous cleavage occurs and is readily reversible. We have discovered that small RNAs derived from this molecule are able to efficiently circularize and are thus capable of producing constructs of self-circularizing RNAs of known size. In addition, mixtures of linear and circular RNAs can be completely resolved using a novel two-dimensional polyacrylamide gel electrophoresis system.

In accordance with this discovery, it is an object of the invention to provide a simple, convenient method for the synthesis of circular RNAs.

It is also an object of the invention to provide a method for the fractionation of mixtures of linear and circular RNAs by polyacrylamide gel electrophoresis.

Other objects and advantages will become readily apparent from the following description.

BRIEF DESCRIPTION OF THE DRAWINGS

FIG. 2 illustrates a two-dimensional polyacrylamide gel electrophoresis system (Panel A) and the analysis of circular RNAs utilizing the system under denaturing conditions (Panel B).

DETAILED DESCRIPTION OF THE INVENTION

The novel process for preparing circular RNAs requires a plasmid containing sequences having the capability of spontaneous cleavage and self-circularization and a promoter for RNA polymerase. In the model system described herein, the pT7 (-) miniM$_{n=36}$ plasmid was found to meet those requirements. This system is presented for description purposes only and is not intended as limiting in any way. Any plasmid which meets these requirements is expected to successfully produce circular RNAs. In addition, the techniques described are known in the recombinant art and are thus expected to be within that level of skill.

The pT7(-)miniM$_{n=36}$ plasmid has been previously described (Feldstein and Bruening. 1993. *Nucleic Acids Res.* vol. 21, pp. 1991–1998, herein incorporated by reference). Essentially, the plasmid contains a cDNA copy of the paperclip ribozyme from satTRSV(-)RNA modified to contain a 36-nucleotide polylinker loop which separates the ribozyme and substrate portions of the satellite RNA (see FIG. 1). Used in the context of the novel process, this loop contains sites at which a DNA fragment may be inserted to produce a circular RNA of known size upon cleavage. The cDNA copy of the paperclip portion of satTRSV(−)RNA thus comprises a minimonomer containing an inserted DNA fragment.

The novel process is thus carried out by first inserting the DNA fragment into the polylinker contained in the minimonomer portion of the pT7 plasmid (see Example 1), and resulting clones are selected for size. An effective means for such selection is by polymerase chain reaction (PCR) amplification (see Example 2).

RNA transcripts are then prepared from selected clones. At this step cleavage and circularization also occur, and clones which effectively circularize are selected. An effective screening method is by denaturing electrophoresis.

Exact sizing of the RNAs is accomplished by sequencing the corresponding cloned cDNAs. The size of the RNA is determined by the size of the DNA iserted into the polylinker sequence, and the reversible nature of the ribozyme cleavage generates a mixture of both linear and circular molecules.

Figure 2A:
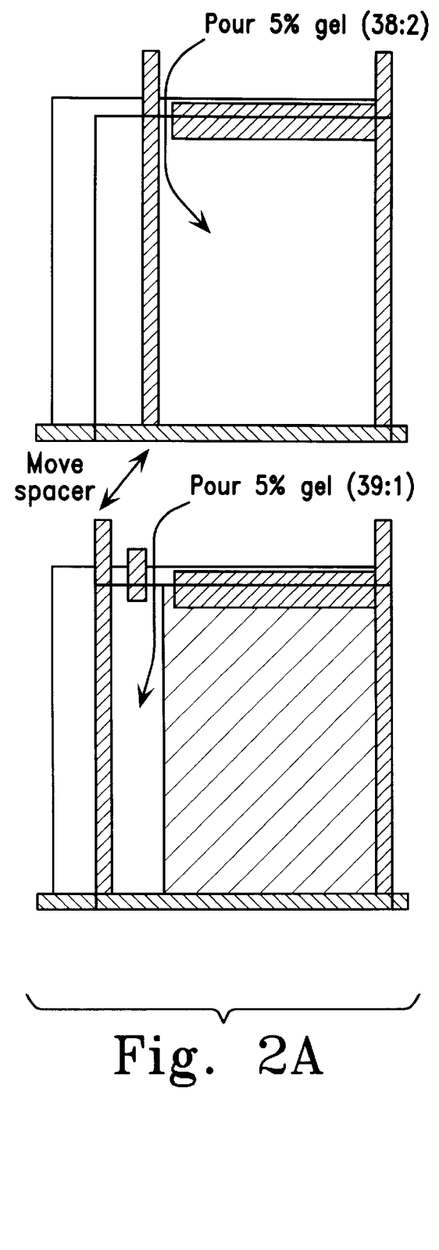
Figure 2B:
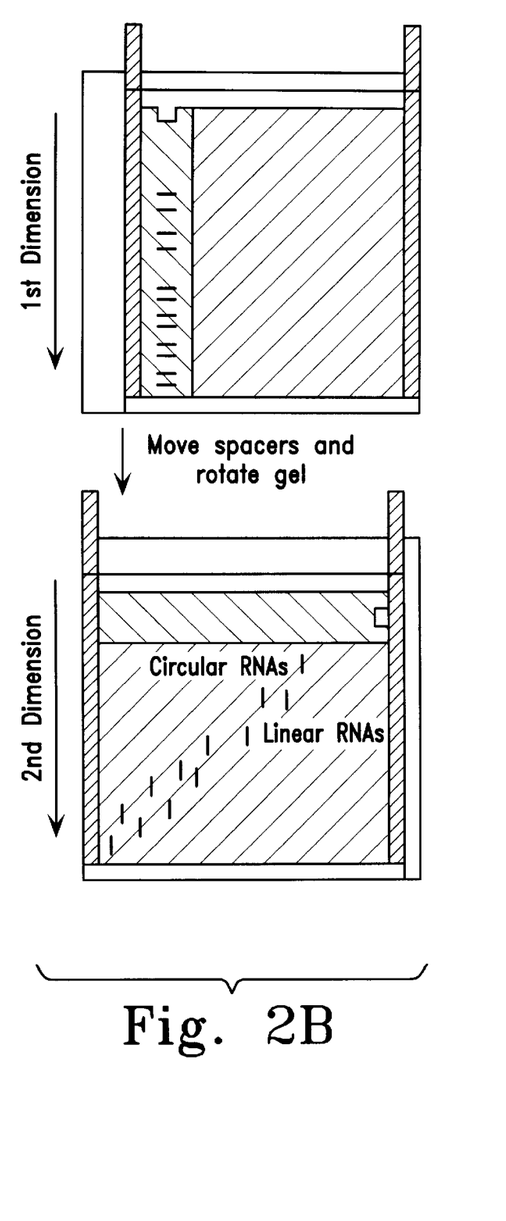

In the novel two-dimensional gel system, the second dimension is more highly cross-linked than the first. In each dimension, the migration rate of a single-stranded RNA molecule is determined by both its size and conformation. Linear molecules migrate faster than the corresponding circular forms, and this effect leads to a pattern of spots in which each linear RNA is found diagonally below the corresponding circular form (see FIG. 2). Thus accurate sizing of the linear and circular forms of RNAs can be accomplished.

The analysis is carried out under denaturing conditions where only noncovalent bonds are affected. The two-dimensional gel is prepared as described in Example 4 and shown in FIG. 2. A first portion of polyacrylamide solution is cast between glass plates as the second dimension using spacers to define the boundaries of this portion of the gel. After sufficient time for polymerization to occur, a spacer is moved such that an additional strip adjacent to the gel is available for casting the first dimension, a strip of a size sufficient for one sample lane. The top edge of the first dimension strip contains a single sample well. Since the second dimension is more highly cross-linked than the first, acrylamide:bis-acrylamide ratio is adjusted accordingly and dependant upon the size of the RNAs to be separated. Ratios of about 39:1 for the first dimension and 38:2 for the second have been found effective, using a polyacrylamide solution of about 5%.

The gel assembly is mounted in a vertical electrophoresis apparatus, the reservoirs filled with buffer, and the gel prerun until the surface of the glass plate cover reaches a predetermined temperature.

A sample containing a mixture of RNAs is dissolved in denaturing buffer containing bromphenol blue and xylene cyanol, heated and applied to the well at the top of the first, less highly crosslinked dimension of the gel.

Power is applied and adjusted to maintain a temperature sufficient for denaturation of the sample to be maintained for electrophoresis in the first dimension. After the xylene cyanol has migrated across a sufficient portion of the gel (about 75–80%), the gel is rapidly rotated 90°, and electrophoresis is continued until the xylene cyanol marker is slightly above the bottom of the gel (about 20 mm).

Figure 1:
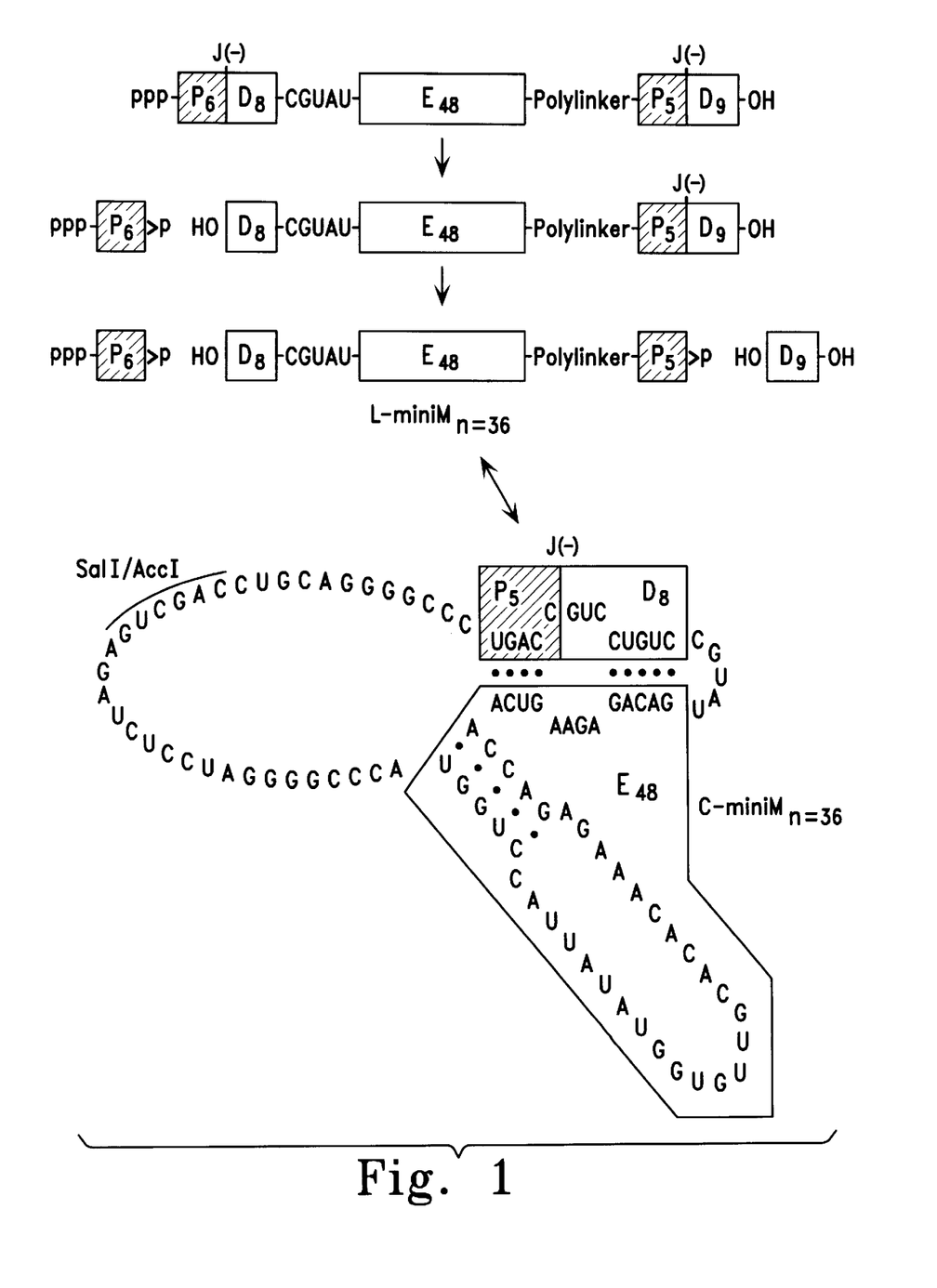
FIG. 1 illustrates minimonomer RNAs derived from sat TRSV(-)RNA.

In the model system described herein, modifications of satTRSV(−)RNA resulted in molecules (or minimonomers) containing little more than covalently attached ribozyme and substrate cleavage products separated by a polylinker sequence. Like naturally occurring satTRSV(−)RNA, such RNAs (e.g. miniM$_{n=36}$) not only undergo spontaneous cleavage in vitro but also readily ligate to form both linear dimers and circular molecules. FIG. 1 shows a schematic representation of the initial RNA transcript (top), one of two partial cleavage products (middle) and fully processed miniM$_{n=36}$ RNA (bottom), SEQ ID NO: 1. The spontaneous circularization of the fully processed linear RNA results in a mixture of linear and circular molecules. P6, D8, P5 and D9 (boxed) denote nucleotides either proximal (P) or distal (D) to the cleavage sites [i.e. J(−)] in the substrate portions of the RNA. The top portion of the circularized molecule is oriented in the 5'→3' direction and shaded areas denote the 48 nt comprising the paperclip ribozyme portion of the RNA.

The initial full-length RNA transcript from miniM$_{n=36}$ thus contains 48 nt of ribozyme—and 36 nt of polylinker-derived sequence flanked by two cleavage-ligation sites. Successive cleavages at the 5' and 3' cleavage sites release a linear 102 nt RNA (L-miniM$_{n=36}$), which then undergoes spontaneous ligation to form the corresponding circular RNA (C-miniM$_{n=36}$) in an equilibrium denoted by the double headed arrow. In experiments carried out to increase the size of the minimonomer RNA transcript, two different types of DNA fragments, either MspI fragments of pBR322 or Sau3AI fragments of λ DNA, were inserted into the unique AccI/SalI recognition site (GTCGAC) of miniM$_{n=36}$.

Approximately 70 clones containing varying sizes and numbers of MspI fragments and a comparable number of additional clones containing Sau3AI fragments of λ DNA were screened by bacterial colony miniprep PCR in order to identify inserts having the desired sizes. Because M13 primers used in the PCR analysis bind outside the satTRSV cDNA sequences, each PCR product was ~100 bp larger than the corresponding minimonomer RNA. Based upon the size and homogeneity of their respective PCR products, a collection of eight clones was assembled for further evaluation. The exact sizes of the minimonomer RNAs, as determined by dye terminator sequence analysis of their respective cDNA templates, ranged from 225 to 1132 nt.

Thus, advantage was taken of the overlapping SalI/AccI sites present in the polylinker sequence separating the ribozyme and substrate portions of the molecule to create the series of self-circularizing RNAs containg 225–1132 nt. It is understood, however, that other sites may be incorporated into the polylinker sequence, either in addition to or instead of the SalI/AccI sites, depending upon the DNA one intends to insert. Following purification by preparative PAGE, linear minimonomer RNAs can be circularized by a brief incubation in the same Tris, Mg$^{2+}$, spermidine buffer used for the initial T7 transcription and ribozyme cleavage.

In contrast to oligodeoxynucleotide-directed RNA ligation (Moore and Sharp. 1992. Science. vol. 256, pp. 992–997; Beaudry and Perrault, supra), interconversion of the linear and circular forms of the modified satTRSV(−) RNAs is both rapid and spontaneous. No lengthy incubation with DNA or RNA ligase or subsequent purification to remove template oligonucleotide is required. Unlike methods involving in vitro rearrangement of group I or group II introns (see, for example, Ford and Ares. 1994. Proc. Natl. Acad. Sci. USA. vol. 91, pp. 3117–3121; Puttaraju and Been. 1996. J. Biol. Chem. vol. 271, pp. 26081–26087), only a single DNA template is required to produce each pair of linear and circular RNAs. While the RNAs studied ranged in size from 225 to 1132 nt, it is contemplated that even larger molecules that retain the ability to spontaneously circularize can be constructed. An important practical limitation is the ability of polyacrylamide gel electrophoresis system to resolve large RNA molecules.

The RNA circularization products were evaluated using the two-dimensional PAGE system. As previously described, both dimensions of the gel system contain 5% polyacrylamide, but with different degrees of cross-linking (see FIG. 2A). The behavior of a mixture of six pairs of linear and circular RNAs in such a gel system is illustrated in FIG. 2B. In the first dimension migration rates of single-stranded RNAs are determined by both their size and conformation. Note that the linear form of each RNA migrates faster than the circular form. In the second dimension, this effect leads to the appearance of each linear RNA in a position diagonally below its corresponding circular form.

Figure 3:
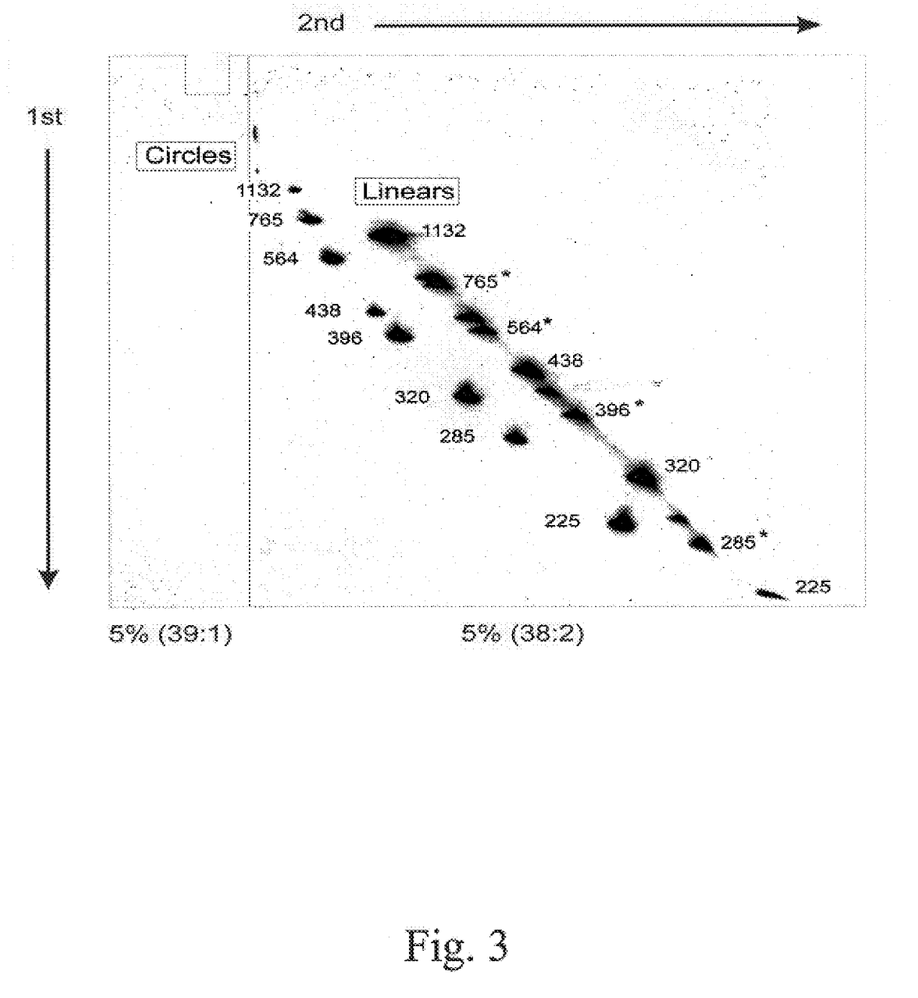
FIG. 3 shows the two-dimensional gel electrophoresis of minimonomer RNAs.

This effect is shown more clearly in the experimental data of FIG. 3. Following synthesis and self-cleavage in the presence of [$\alpha$-$^{32}$P]CTP, linear RNAs (either the fully processed minimonomer or a mixture of the fully processed minimonomer and minimonomer/D partial cleavage product) were purified by one-dimensional electrophoresis under denaturing conditions. One-dimensional electrophoresis under denaturing conditions (i.e. 1× TBE buffer, 7 M urea at 50° C.) revealed differences in the processing efficiencies of eight selected minimonomer RNAs. Molecules containing 225, 320 or 428 nt processed efficiently, and the fully processed linear minimonomers were excised from the gel, eluted in 0.5 M NH$_4$ acetate, 0.1% SDS and recovered by ethanol precipitation. For those RNAs which processed less efficiently, mixtures of the fully and partially processed minimonomer (see FIG. 1) were recovered instead. Purified RNAs were then mixed and incubated under conditions suitable for self-ligation before fractionation by two-dimensional gel electrophoresis. Positions of the circular and linear forms of each minimonomer are indicated. The four linear RNAs (denoted by asterisks) produced duplicate spots; in each case the more slowly migrating spot contains uncleaved minimonomer/D precursor.

Eight circular molecules ranging in size from 225 to 1132 nt were clearly resolved, both from each other and from the corresponding linear molecules. The pattern of linear RNAs present on the second (i.e. more rapidly migrating) diagonal, where at least 12 separate spots are visible, was slightly more complex. The most rapidly moving spot, barely visible as it exits the gel at the lower right hand corner, contains the 225 nt RNA; positions of the other seven fully processed minimonomer RNAs are also marked.

Experiments were carried out in order to confirm the utility of the system by resolving different sizes of naturally-occurring circular RNA molecules. Extracts from coconut palms infected with coconut cadang-cadang viroid (CCCVd) contain a complex mixture of monomeric and multimeric viroid RNAs (Randles, J. 1985. In Maramorosch and and McKelvey, eds. *Subviral Pathogens of Plants and Animals: Viroids and Prions*. Academic Press, Orlando, Fla., pp. 39–74). As the disease progresses the "fast" forms of CCCVd which predominate during the early stages of infection are replaced by "slow" forms (Imperial et al. 1981. *J. Gen. Virol.* vol. 56, pp. 77–85). Nucleotide sequence analysis suggests that the slow (i.e. 296–297 nt) form of monomeric CCCVd RNA is directly derived from the corresponding 246–247 nt fast form by a sequence duplication event involving the right hand portion of the molecule (Haseloff et al. 1982. *Nature*. vol. 299, pp. 316–321).

Figure 4:
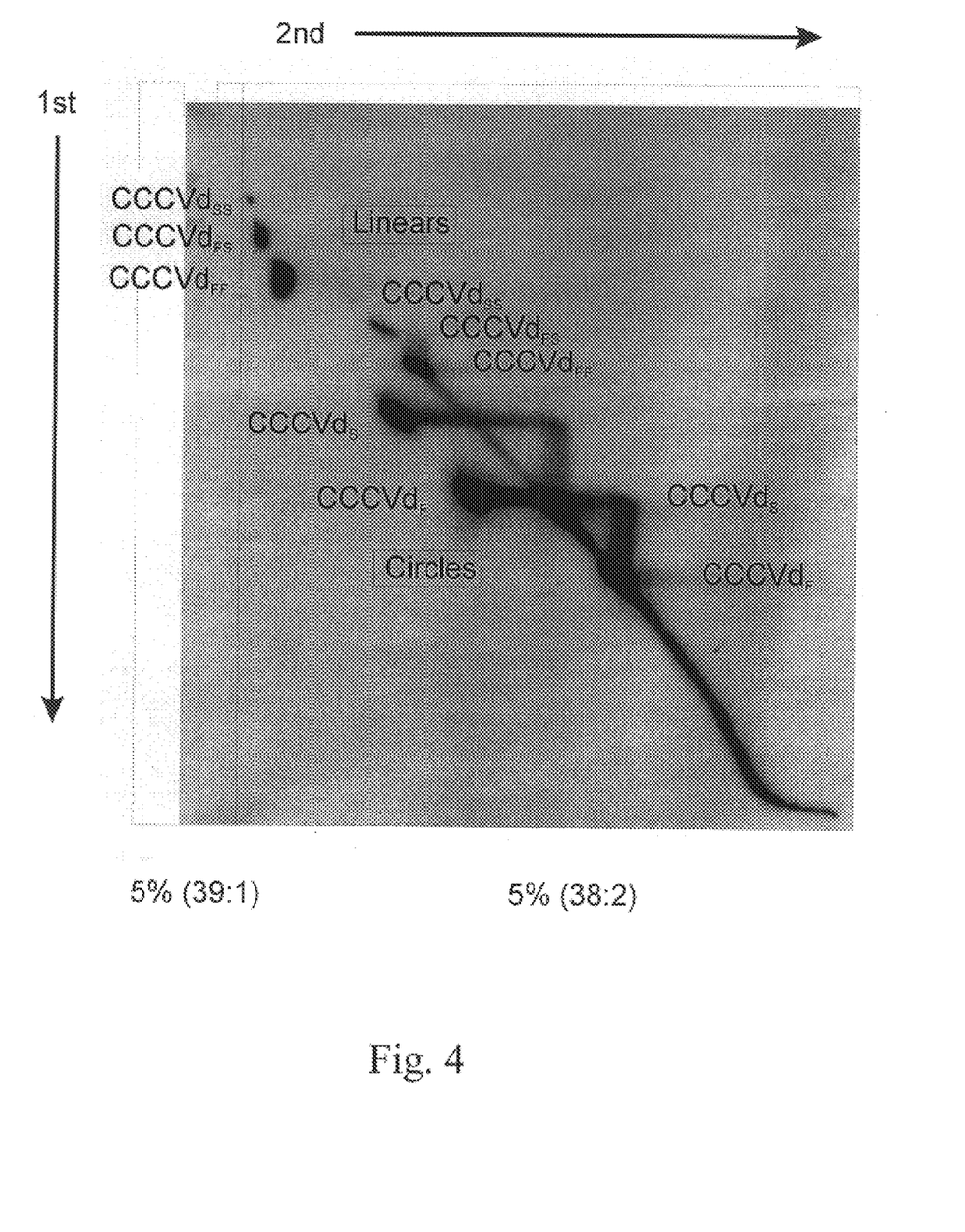
FIG. 4 shows the two-dimensional gel electrophoresis of a complex mixture of monomeric and dimeric viroid RNAs present in coconut cadang—cadang viroid-infected palms.

FIG. 4 shows the resolution of linear and circular (+)CCCVd RNAs possible using the two dimensional system. Unlabeled CCCVd RNAs were fractionated by two-dimensional electrophoresis and transferred to a positively-charged nylon membrane before hydridization with a $^{32}$P-labeled RNA probe complementary to CCCVd. In addition to circular and linear forms of the monomeric fast (CCCVd$_F$, 246–247 nt) and slow (CCCVd$_S$, 296–297 nt) forms of CCCVd RNAs, three different dimeric RNAs could also be resolved, i.e. fast-fast (CCCVd$_{FF}$), fast-slow (CCCVd$_{FS}$) and slow-slow (CCCVd$_{SS}$) molecules. Note the presence of streaks extending first horizontally, then vertically from the circular forms of CCCVd$_F$ and CCCVd$_S$ to their respective linear forms. These streaks (or cross-peaks) contain linear molecules produced by cleavage during electrophoresis in either the second or first dimension. Longer autoradiographic exposures revealed similar streaks connecting the more slowly moving fast-fast (CCCVd$_{FF}$), fast-slow (CCCdv$_{FS}$) and slow-slow (CCCVd$_{SS}$) circular dimeric RNAs with their respective linear forms (data not shown). Likewise, the continuous "diagonal" connecting the linear CCCVd RNAs can be explained by random degradation, either before electrophoresis or during the first dimension. Long autoradiographic exposures revealed the presence of similar cross-peaks and diagonals in gels containing $^{32}$P-labeled minimonomer RNAs synthesized in vitro (results not shown).

Electrophoresis in polyacrylamide gels containing high concentrations of ureas has been widely described for both the analysis and purification of RNA under denaturing conditions (Maniatis et al., supra). One dimensional electrophoresis under such conditions is sufficient to separate the 359 nt circular and linear forms of potato spindle tuber viroid (Gross et al. 1978. *Nature*. vol. 273, pp. 203–208), but a variety of other two-dimensional (see, for example, DeWachter and Fiers. 1982. In Rickwood and Hames, eds. *Gel Electrophoresis of Nucleic Acids: A Practical Approach*. IRL Press, Washington, D.C., pp. 77–116) and bidirectional (Schumacher et al., 1983, supra; Schumacher et al., 1986, supra) gel systems have also been described for fractionation of complex mixtures of RNAs to high levels of purity. Most two-dimensional systems are based on the effects of increasing the concentration of either acrylamide or urea between the first and second dimension. Increases in acrylamide concentration (usually in the ratio of 1:2) have often been used to separate RNAs containing 50–500 nt, but changes in the concentrations of both acrylamide and urea can also be combined in a single system (Ikemura, T. 1989. *Methods Enzymol*. vol. 180, pp. 14–25).

The novel system described herein, however, relies upon an increase in the degree of crosslinking rather than acrylamide concentration to preferentially retard migration of circular molecules. In its present configuration (i.e. 5% polyacrylamide with an acrylamide:bis-acrylamide ratio of 38:2 in the second dimension) this gel system is able to resolve circular and linear RNAs containing as many as 1100–1200 nt. For many two-dimensional systems, it is necessary to excise the relevant portion of the first dimension gel before polymerization of the second dimension gel. Because the buffer conditions are identical (i.e. 1×TBE, 7 M urea), it is convenient and reproducible to cast both dimensions of the gel before applying the sample, then simply rotate the gel between the first and second dimensions. Analysis of larger RNAs requires gels with increased pore size that still retain adequate mechanical strength to allow visualization of the various molecular species by autoradiography or staining. Agarose gel electrophoresis of glyoxal-denatured RNAS (McMaster and Carmichael. 1977. *Proc. Natl. Acad. Sci. USA*. vol. 74, pp. 4835–4838) provides one possible approach.

The use of denaturing conditions in both dimensions of our gel system allows certain linear RNAs to be identified as products of intragel cleavage or their respective circular forms. The resulting cross-peak phenomenon allows identification of sets of linear and circular RNAs and can provide a considerable analytical advantage over other gel systems where the first dimension is non-denaturing and the second denaturing. For example, the linear and circular forms of the previously undescribed fast-slow heterodimer among the CCCVd RNAs (analyzed in FIG. 4) was identified. The general accepted rolling circle model for viroid replication (Branch and Robertson. 1984. *Science*. vol. 223, pp. 450–455) readily explains the presence of fast-fast and slow-slow CCCVd monomers in infected trees, but this model does not predict synthesis of large amounts of heterodimeric fast-slow CCCVd RNA (see Haseloff et al., supra).

The circular RNAs are useful as molecular markers when included in mixtures of unknown RNAs. For example, marker and sample RNAs may be separately labeled with different labels (such as, for example, radioactive and fluorescent labels) and run in the same gel, providing the capability to compare the mobility of the RNAs under investigation to those of a series of linear and circular RNA standards. This allows the convenient and accurate sizing of naturally-occurring linear and circular RNAs, thus improving the ability to detect and identify a variety of small pathogenic RNAs. This will facilitate studies of circular RNAs associated with certain human and animal diseases and the abnormal processing of cellular messenger RNAs.

The following examples are intended only to further illustrate the invention and are not intended to limit the scope of the invention which is defined by the claims.

EXAMPLES

Example 1
Construction of satTRSV Minimonomer cDNAs.

DNA inserts were ligated into pT7(−)miniM$_{n=36}$, a plasmid containing a cDNA copy of a specially modified version of the paperclip ribozyme from satTRSV(−)RNA, the less abundant form of sat TRSV RNA (Feldstein and Bruening, supra). Clones designed to yield minimonomer RNAs containing <400 nt were generated by ligating Sau3A fragments of λ DNA into SalI-digested vector. Prior to ligation, inserts and vector were made compatible by two base fill-in reactions using the Klenow fragment of *Escherichia coli* DNA polymerase I and dGTP/dATP or dTTP/dCTP, respectively. Clones yielding minimonomer RNAs containing 420–1132 nt were generated by ligating MspI-digested pBR322 (Pharmacia, Piscataway, N.J.) directly into AccI-digested pT7(−)miniM$_{n=36}$.

Example 2
Screening for Insert Size by PCR.

Clones were screened for insert size using a PCR colony miniprep precedure and the M13 universal forward, 5'-GTAAAACGACGGCCAGT-3' (SEQ ID NO: 2), and reverse-5, 5 '-CAGGAAACAGCTATGA-3' (SEQ ID NO: 3), sequencing primers (Feldstein and Bruening, supra; Leonard et al. 1989. *BioTechniques*. vol. 7, p. 7). PCR products were analyzed on 5% polyacrylamide gels containing 1×TBE buffer (89 mM Tris, 89 mM borate, 2.5 mM Na$_2$EDTA, pH 8.3) and visualized by staining with silver nitrate. Insert size was verified by automated dye terminator sequencing (Applied Biosystems, Foster City, Calif.).

Example 3
Transcription, Self-Cleavage and Circularization of Minimonomer RNAs.

$^{32}$P-labeled minimonomer RNAs were prepared by in vitro transcription of selected PCR products (2.0 μl) in 10-μl reaction mixtures conatining 1× transcription buffer (10 mM Tris, 15 mM MgCl$_2$, 2 mM spermidine-HCl, pH 7.5), 10 mM DTT, 10 U RNasin (Promega, Madison, Wis.), 2.5 mM rNTPs (rGTP, rATP, and rUTP), 100 μM rCTP, 5–10 μCi [α-$^{32}$P]rCTP (800 Ci/mmol; Amersham) and 20 U T7 RNA polymerase (New England Biolabs). Reactions were incubated for 2 h at 37° C. and then heated for 2 min at 100° C. following addition of 5 μl sequencing stop buffer (10 mM NaOH, 95% formamide, 0.05% bromophenol blue, 0.05% xylene cyanol).

Denatured RNAs were loaded onto a pre-run 5% polyacrylamide gel containing 1×TBE buffer, 7 M urea and electrophoresed until the xylene cyanol dye had reached the bottom of the gel. Bands containing the desired $^{32}$P-labeled minimonomer RNAs were identified by autoradiography and recovered by the crush and soak method (Sambrook et al. 1989. *Molecular Cloning: A Laboratory Manual.* Cold Spring Harbor Laboratory Press, Cold Spring Harbor, N.Y., p. 646). Gel-purified linear RNAs were allowed to circularize by addition of an equal volume of 2× transcription buffer and incubation at 37° C. (10 min) and 0°C. (30 min). The reaction was stopped by addition of an equal volume of sequencing stop buffer.

Example 4
Two-Dimensional Polyacrylamide Gel Electrophoresis.

One plate from each pair of 5 mm thick glass plates used to cast polyacrylamide slab gels was larger than the other, i.e. 183×183 mm vs. 176×176 mm. The inward facing surface of the smaller plate was siliconized, and the plates were arranged as shown in FIG. 2A. Two plexiglass spacers (8 mm wide, 1 mm thick) were inserted in alignment with the flush edges of the plates, and a third spacer was placed with its outer edge 22–25 mm from the edge of the smaller plate. A 5% polyacrylamide gel (acrylamide:N,N'-methylene bis-acrylamide 38:2) containing 1×TBE, 7 M urea was then cast to a level 8 mm below the edge of the smaller plate. Following polymerization, the third spacer was moved to the edge of the smaller plate and a 5% polyacrylamide gel (acrylamide:N,N'-methylene bis-acrylamide 39:1) containing 7M urea and 1×TBE buffer was then cast in the resulting space. As shown in FIG. 2B, the top edge of this gel contained a single sample well that is ~10 mm deep.

Following removal of spacer 2, the gel assembly was mounted in a vertical electrophoresis apparatus, the reservoirs filled with 1×TBE buffer, and the gel prerun at 50 mA (~400 V) until the surface of the outer glass plate reached a constant 50° C. The RNA sample was dissolved in 40 μl 50% formamide, 5 mM Tris-HCl, pH 7.5, 0.5% SDS, 0.05% (each) bromophenol blue and xylene cyanol and heated at 90° C. for 3 min immediately before application to the single well at the top of the first dimension (i.e. less highly crosslinked) gel. Power was then reapplied and adjusted to maintain a temperature of 50° C. (thereby ensuring continued sample denaturation) during electrophoresis in the first dimension. After the xylene cyanol had migrated 140 mm, the gel assembly was removed from the apparatus in order to rearrange, as quickly as possible, spacers 1 and 3. As shown in FIG. 2B, the gel assembly was rotated 90° during remounting. Electrophoresis was continued in the second dimension until the xylene cyanol was ~20 mm from the bottom of the gel.

The gel was then immediately removed from between the glass plates and processed in one of two ways. For $^{32}$P- labeled RNAs, the gel was fixed in 10% ethanol, 1% acetic acid and dried on filter paper prior to autoradiography. Alternatively, the RNAs were transferred to positively charged nylon membrane (Nytran Plus; Schleicher & Schuell) using a semi-dry Transblotter (BioRad) and freshly prepared transfer buffer (102.5 ml 40 mM MOPS, pH 7.0, 10 mM Na acetate, 1 mM EDTA+22 ml 37.5% formaldehyde). For the analysis of CCCVd RNAs, a preparation of unlabeled CCCVd RNAs approximately equimolar for the 246, 247, 296 and 297 nt forms of the viroid and also containing their respective dimers was provided by Dr. M. J. B. Rodriquez (Philippine Coconut Authority, Guinobata, Philippines). Electrotransfer was carried out for 30–40 min at 0.3 nA/cm$^2$, and the transferred nucleic acids were crosslinked to the nylon membrane with 20,000 μJ/cm$^2$ UV light using a Stratalinker 1800 apparatus (Stratagene, LaJolla, Calif.). Prehybridization and hybridization reactions were carried out as previously described (Hanold and Randles. 1991. *Annls Appl. Biol.* vol. 118, pp. 139–151) using a $^{32}$P-labeled full-length cRNA probe specific for CCCVd.

All references cited hereinabove are herein incorporated by reference.

We claim:

1. A method for making circular RNAs, said method comprising a) inserting a DNA fragment into a plasmid containing a cDNA having an insertion site effective for DNA insertion, sequences capable of spontaneous cleavage and circularization and a promoter for RNA polymerase, b) selecting one or more clones resulting from step a) according to the size of the inserted DNA, c) preparing RNA transcripts from selected clones, during which said spontaneous cleavage and circularization occur, and d) selecting RNAs which effectively circularize.

2. The method of claim 1, wherein said plasmid is derived from satellite tobacco ringspot virus(−)RNA.

3. The method of claim 2, wherein said plasmid comprises a cDNA of the ribozyme portion of said satellite tobacco ringspot virus(−)RNA and wherein said cDNA contains a polylinker loop separating the ribozyme and substrate portions of the satellite RNA and an insertion site effective for the insertion of said DNA fragment.

4. The method of claim 1, wherein said DNA fragment inserted into the plasmid at step a) is of a known size.

5. The method of claim 4, wherein said plasmid is derived from satellite tobacco ringspot virus(−)RNA.

6. The method of claim 5, wherein said plasmid comprises a cDNA of the ribozyme portion of said satellite tobacco ringspot virus(−)RNA and wherein said cDNA contains a polylinker loop separating the ribozyme and substrate portions of the satellite RNA and an insertion site effective for the insertion of said DNA fragment.

* * * * *

UNITED STATES PATENT AND TRADEMARK OFFICE
CERTIFICATE OF CORRECTION

PATENT NO.     : 6,210,931 B1                                             Page 1 of 1
DATED          : April 3, 2001
INVENTOR(S)    : Paul A. Feldstein et al.

It is certified that error appears in the above-identified patent and that said Letters Patent is hereby corrected as shown below:

<u>Title page,</u>
Item [73], Assignee, should read as:

-- [73]  Assignees:  University of Maryland, College Park, Md,; The United States of America as represented by the Secretary of Agriculture, Washington, D.C. --

Signed and Sealed this

Fifteenth Day of April, 2003

JAMES E. ROGAN
*Director of the United States Patent and Trademark Office*